US00PP24149P3

(12) United States Plant Patent

Davey et al.

(10) Patent No.: US PP24,149 P3

(45) Date of Patent: Jan. 7, 2014

(54) ***HELLEBORUS* PLANT NAMED 'ABCRD01'**

(50) Latin Name: *Helleborus×hybridus*
Varietal Denomination: ABCRD01

(75) Inventors: Rodney Davey, Devon (GB); Lynda Christine Windsor, Devon (GB)

(73) Assignees: Rodney Davey, Devon (GB); Lynda Windsor, Devon (GB)

( * ) Notice: Subject to any disclaimer, the term of this patent is extended or adjusted under 35 U.S.C. 154(b) by 186 days.

(21) Appl. No.: 13/374,191

(22) Filed: Dec. 15, 2011

(65) Prior Publication Data

US 2013/0160174 P1 Jun. 20, 2013

(51) Int. Cl.
*A01H 5/00* (2006.01)
*A01H 5/02* (2006.01)

(52) U.S. Cl.
CPC ..... *A01H 5/02* (2013.01)
USPC ..... Plt./439

(58) Field of Classification Search
USPC ..... Plt./439
See application file for complete search history.

*Primary Examiner* — June Hwu
*Assistant Examiner* — Louanne Krawczewicz Myers
(74) *Attorney, Agent, or Firm* — Jondle Plant Sciences Division Swanson & Bratschun, L.L.C.

(57) ABSTRACT

A new *Helleborus* plant particularly distinguished by abundant red-purple flowers, upright plant habit and a vigorous growth habit, is disclosed.

1 Drawing Sheet

Genus and species: *Helleborus×hybridus.*
Variety denomination: 'ABCRD01'.

BACKGROUND OF THE NEW PLANT

The present invention comprises a new and distinct variety botanically known as *Helleborus×hybridus*, and hereinafter referred to by the variety name 'ABCRD01'. The new variety originated from a controlled hybridization conducted in February 2007 in Devon, United Kingdom, between female hellebore plant *Helleborus* nr. 3469RDEX2 (unpatented) and male hellebore plant *Helleborus* nr. 3465RDMT45 (unpatented). The seeds produced by the hybridization were sown in Devon, United Kingdom at RD Plants Company. A single plant selection was chosen for further evaluation and for asexual propagation in Devon, United Kingdom.

'ABCRD01' was subsequently asexually propagated by tissue culture in Aalsmeer, The Netherlands for 3 years. The present invention has been found to retain its distinctive characteristics through successive asexual propagations for at least 50 generations.

Community Plant Variety Rights (CPVR) for this variety were applied for in Europe on Oct. 25, 2011. 'ABCRD01' has not been made publicly available more than one year prior to filing of this application.

SUMMARY OF THE INVENTION

The following are the most outstanding and distinguishing characteristics of this new variety when grown under normal horticultural practices in Aalsmeer and Boijl, The Netherlands.

1. Abundant, red-purple flowers;
2. Upright plant habit; and
3. A vigorous growth habit.

DESCRIPTION OF THE PHOTOGRAPH

This *Helleborus* plant is illustrated by the accompanying photograph which shows overall plant habit including blooms, buds, and foliage of the plant; the colors shown are as true as can be reasonably obtained by conventional photographic procedures. The photograph is of a whole plant about one-year-old, grown outdoors in Boijl, The Netherlands.

DESCRIPTION OF THE NEW VARIETY

The following detailed description sets forth the distinctive characteristics of 'ABCRD01'. The data which define these characteristics were collected from asexual reproductions carried out in Aalsmeer and Boijl, The Netherlands. The plant history was taken on one-year-old plants grown outdoors. Color readings were taken under artificial light. Color references are primarily to The R.H.S. Colour Chart of The Royal Horticultural Society of London (R.H.S.) (2001).

DETAILED BOTANICAL DESCRIPTION

Classification:
- *Family.*—Ranunculaceae.
- *Genus and species.*—*Helleborus×hybridus.*
- *Common name.*—Christmas Rose.
- *Variety name.*—'ABCRD01'.

Plant:
- *Plant and growth habit.*—Upright and vigorous.
- *Propagation.*—In vitro propagation by tissue culture.
- *Height.*—25.0 cm to 35.0 cm.
- *Width.*—20.0 cm to 25.0 cm.
- *Time to initiate roots.*—6 weeks.
- *Time to produce a rooted cutting.*—Approximately 3 months.
- *Time to produce a finished plant.*—3 months.
- *Root habit.*—Vigorous and fleshy roots.

Stems:
- *Shape.*—Compact.
- *Length.*—3.0 cm.
- *Diameter.*—2.0 cm.
- *Internode length.*—0.1 cm.

*Texture*.—Smooth.
*Color*.—RHS 183C.

Leaves:
*Type*.—Palmately compound.
*Arrangement*.—Alternate.
*Length*.—15.0 cm to 20.0 cm.
*Width*.—15.0 cm to 20.0 cm.
*Shape*.—Ovate.
*Apex*.—Obtuse.
*Base*.—Acute.
*Margin*.—Serrate.
*Texture* (*both upper and lower surfaces*).—Smooth.
*Color* (*both immature and mature leaves*).—Upper surface: RHS 139A. Lower surface: RHS 138A.
*Venation pattern*.—Longitudinal.
*Venation color* (*both upper and lower surfaces*).—RHS 138A.
*Venation color* (*at base of leaf*).—Mature leaf: RHS 187A. Immature leaf: RHS 59B.
*Variegation*.—Absent.
*Leaflets*.—Quantity per leaf: 4 to 6. Shape: More cordate than oval. Length: 6.0 cm to 10.0 cm, depending on the growing stage. Width: 4.0 cm to 6.0 cm, depending on the growing stage. Apex: Acute. Base: Between cordate and obtuse. Margin: Serrate.
*Petiole*.—Length: 20.0 cm to 25.0 cm. Diameter: 0.5 cm. Color: RHS 183C. Texture: Smooth.
*Petiolule*.—Length: 2.0 cm. Diameter: 0.5 cm. Color: RHS 183C. Texture: Smooth.
*Stipules*.—Absent.

Inflorescence:
*Type*.—Loosely branched cymes.
*Shape*.—Loosely branched.
*Self cleaning or persistent*.—Persistent.
*Flowering habit*.—Vertical facing flowers above the foliage.
*Flowering season*.—January through February.
*Quantity of inflorescences on the plant*.—10 to 15.
*Fragrance*.—Absent.
*Lastingness of inflorescences on the plant*.—At least 2 months.
*Diameter*.—15.0 cm.
*Depth* (*height*).—30.0 cm.

Flower:
*Type*.—Single.
*Diameter*.—4.0 cm to 5.0 cm.
*Depth* (*height*).—0.8 cm to 1.0 cm.
*Quantity per inflorescence*.—2 to 3.

Bud:
*Height*.—3.0 cm.
*Diameter*.—2.0 cm.
*Shape*.—Ovate.
*Colour*.—RHS 70B.
*Texture*.—Smooth.

Bracts:
*Shape*.—Ovate.
*Quantity per inflorescence*.—2 to 10.
*Length*.—3.0 cm.
*Width*.—2.0 cm.
*Apex*.—Acute.
*Base*.—Ovate.
*Margin*.—Smooth.
*Texture* (*both upper and lower surfaces*).—Smooth.
*Color*.—Upper surface: RHS 139A. Lower surface: RHS 138A.

Peduncle:
*Shape*.—Round.
*Length*.—20.0 cm.
*Width*.—0.5 cm.
*Texture*.—Smooth.
*Color*.—RHS 183B.

Pedicel:
*Length*.—2.0 cm to 5.0 cm.
*Diameter*.—0.3 cm.
*Texture*.—Smooth.
*Color*.—RHS 183B.

Sepals:
*Quantity per flower*.—5.
*Arrangement*.—Single whorl.
*Shape*.—Orbicular.
*Length*.—2.5 cm.
*Width*.—2.5 cm.
*Apex*.—Rounded.
*Base*.—Rounded.
*Margin*.—Smooth.
*Texture* (*both upper and lower surfaces*).—Smooth.
*Color*.—Upper surface: RHS 70B. Lower surface: RHS 70C.

Reproductive organs:
*Stamens*.—Quantity per flower: Greater than 60. Color: RHS 4D. Filament length: 1.5 cm. Filament width: 0.05 cm.
*Anthers*.—Shape: Ovate. Length: 0.2 cm. Diameter: 0.1 cm. Color: RHS 4B. Pollen amount: Sparse. Pollen color: RHS 4B.
*Pistils*.—Quantity per flower: 5. Shape: Tuberculate. Length: 1.5 cm. Width: 0.1 cm. Color: RHS 183A.
*Stigma*.—Length: 0.2 cm. Width: 0.05 cm. Color: RHS 157C.
*Style*.—Length: 0.5 cm to 0.7 cm. Color: RHS 71C.
*Ovary*.—Shape: Ovate. Color: RHS 139A.
*Nectaries*.—Quantity per flower: 10 to 14. Shape: Funnel. Length: 0.5 cm to 0.7 cm. Width: 0.2 cm to 0.3 cm. Color: RHS N144B.

Fruit and seed set: None observed.
Disease and insect resistance: No particular resistance or susceptibility observed.
Physiological characteristics: Tolerant to frost.

COMPARISON WITH COMMERCIAL VARIETIES

'ABCRD01' differs from the commercial variety 'HGP01' (U.S. Plant Pat. No. 21,062) in that 'ABCRD01' has a flower bud color of RHS 70B (red-purple), whereas 'HGP01' has a flower bud color close to RHS 184C (grayed-purple). Additionally, 'ABCRD01' has red-purple sepals (RHS 70B), whereas 'HGP01' has white sepals (RHS 155C) that become closer to pink (RHS 56D) with development.

We claim:

1. A new and distinct variety of *Helleborus* plant as described and shown herein.

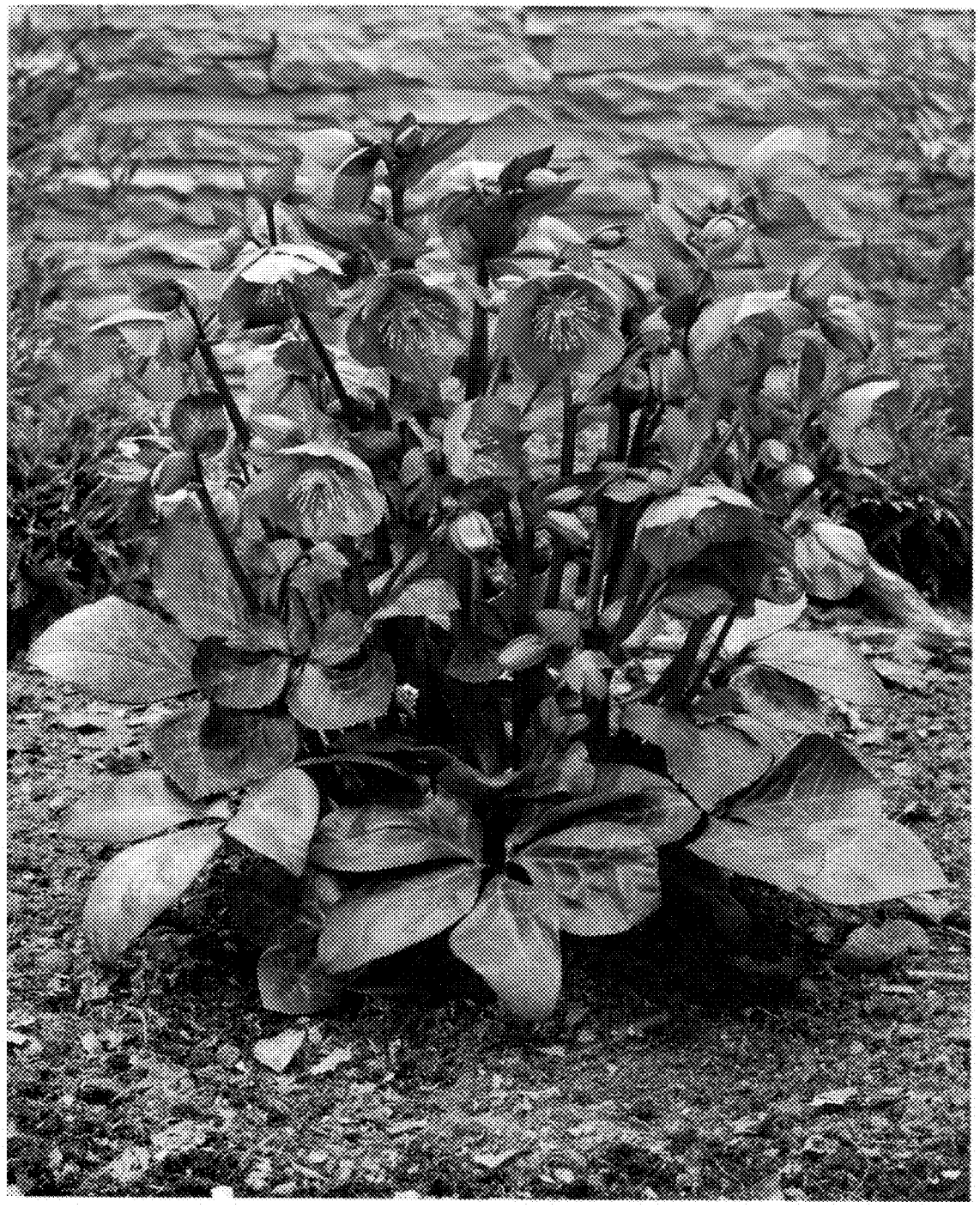

* * * * *